United States Patent [19]

Fuss et al.

[11] Patent Number: 4,756,739
[45] Date of Patent: Jul. 12, 1988

[54] PYRIDINE DERIVATIVES AND THE N-OXIDES THEREOF, AND THE USE THEREOF AS INTERMEDIATES FOR THE SYNTHESIS OF PLANT PROTECTING AGENTS

[75] Inventors: Andreas Fuss, Karlstein; Volker Koch, Kelkheim, both of Fed. Rep. of Germany

[73] Assignee: Hoechst Aktiengesellschaft, Frankfurt am Main, Fed. Rep. of Germany

[21] Appl. No.: 944,547

[22] Filed: Dec. 19, 1986

[30] Foreign Application Priority Data

Dec. 21, 1985 [DE] Fed. Rep. of Germany ....... 3545570

[51] Int. Cl.$^4$ ................ A01N 43/40; C07F 9/28; C07D 213/60; C07D 213/62
[52] U.S. Cl. ................................ 71/87; 71/86; 71/94; 546/22; 546/24; 546/290; 546/293; 546/294; 546/296; 546/297; 546/300; 546/301; 546/302; 546/303; 546/304; 546/307; 546/311; 546/312; 534/616; 534/771
[58] Field of Search ............... 546/293, 296, 300, 297, 546/290, 24, 22, 294, 301, 302, 303, 307, 311, 312, 304; 71/94, 86, 87

[56] References Cited

U.S. PATENT DOCUMENTS 3,810,752 5/1974 Wilcox .............................. 71/94
4,503,061 3/1985 Bristol et al. ..................... 546/303

Primary Examiner—John M. Ford
Assistant Examiner—J. Richter
Attorney, Agent, or Firm—Curtis, Morris & Safford

[57] ABSTRACT

The compounds of the formula I

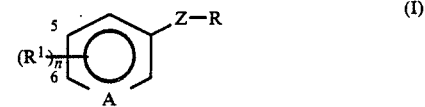

in which A denotes N or N→O, Z denotes O or NH, R denotes H, (halo)alkyl, (halo)alkenyl, (halo)alkynyl or alkoxycarbonyl, R$^1$ denotes hydrogen, halogen, amino, —NHOH, hydroxyl, (substituted) phenylazo or a radical of the formulae Y=C=N—, Y$^1$Y$^2$C=N—, Y$^3$NH— or

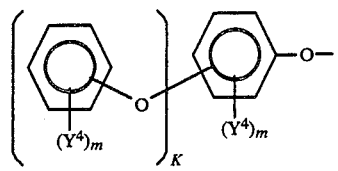

K denotes 0 or 1, and m and n, independently of one another, denote a number from 1 to 4, with the proviso that, when Z-R denotes OH or NH$_2$, (R$^1$)$_n$ denotes at least one radical of the formula

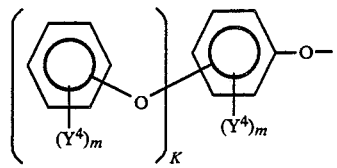

or represents two radicals, in the 5 or 6 position of the heterocyclic ring, which, in the 5 position, denote halogen and, in the 6 position, denote a radical of the group comprising halogen, amino, hydroxyl or phenylazo, which may be substituted as specified above, are valuable intermediates in the synthesis of plant protection agents.

4 Claims, No Drawings

PYRIDINE DERIVATIVES AND THE N-OXIDES THEREOF, AND THE USE THEREOF AS INTERMEDIATES FOR THE SYNTHESIS OF PLANT PROTECTING AGENTS

Hydroxy- and aminopyridine derivatives are known from K. M. Dynmaer and L. D. Smirnov, Russ.Chem.- Rev. 44, 823 (1975), and A. S. Tomcufcik and L. N. Starker in E. Klinsberg, The Chemistry of Heterocyclic Compounds, Volume 14, p. 1-155, Interscience Publishers, Wiley, N.Y. 1962.

The present invention relates to the novel compounds of the formula I

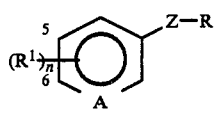     (I)

in which

A denotes N or N→O,

Z denotes O or NH,

R denotes H, halogenated $(C_1-C_8)$alkyl, halogenated $(C_2-C_8)$alkenyl or halogenated $(C_2-C_6)$alkynyl, and, for Z=O, denotes $(C_1-C_4)$alkoxycarbonyl, $R^1$, with an identical or different meaning, denotes hydrogen, halogen, amino, -NHOH, hydroxyl, phenylazo which may be mono- or polysubstituted in the phenyl ring by halogen, nitro, carboxyl, sulfo, $(C_1-C_8)$alkyl, $(C_1-C_8)$alkoxy, halogenated $(C_1-C_8)$alkyl or halogenated $(C_1-C_8)$alkoxy, or denotes a radical of the formulae $Y=C=N-$, $Y^1Y^2C=N-$, $Y^3NH-$ or

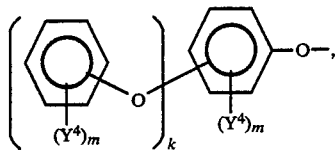

where n preferably denotes 1 for this radical,

Y denotes O or S $Y^1$ denotes halogen, $(C_1-C_3)$alkylthio, $(C_1-C_3)$alkylsulfenyl or $(C_1-C_3)$alkylsulfonyl, $Y^2$ denotes a radical mentioned for $Y^1$ or mercapto, $Y^3$ denotes $(C_1-C_6)$alkyl or $(C_1-C_6)$alkylsulfenyl which may both be halogenated, phenylsulfenyl which may be substituted by $(C_1-C_6)$alkyl, $(C_1-C_6)$alkoxy, $(C_1-C_6)$alkoxycarbonyl, halo$(C_1-C_6)$alkyl, halo$(C_1-C_6)$alkoxy, halo$(C_1-C_6$-alkyl)carbonyl, halogen, nitro or cyano, or denotes phosphoryl or thiophosphoryl which may both be substituted by two radicals from the group comprising $(C_1-C_8)$alkoxy, $(C_1-C_6)$alkylthio, amino, $(C_1-C_6)$alkylamino or di$(C_1-C_6$ alkyl)amino, $Y^4$ independently of one another, denote H, halogen, $NO_2$, $NH_2$, $-NHY^3$, $-NHOH$, $-NCO$, $-NCS$, OH, $(C_1-C_6)$alkyl, $(C_2-C_6)$alkenyl, $(C_2-C_6)$alkynyl, $(C_1-C_6)$alkoxy or $(C_1-C_6)$alkoxycarbonyl, where the last five radicals mentioned may be halogenated, or denote nitro, cyano, carboxyl or a carboxylate salt, K denotes 0 or 1, m and n, independently of one another, denote a number from 1 to 4, with the proviso that n does not denote O when Z-R denotes OH or $NH_2$, and at least one radical $R^1$ denotes a radical of the formula

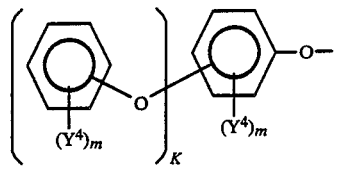

or $(R^1)_n$ represents two radicals in the 5 or 6 position of the heterocyclic ring, whereby in the 5 position $R^1$ is halogen and in the 6 position $R^1$ is a radical of the group comprising halogen, amino, hydroxyl or phenylazo, which is unsubstituted or substituted as mentioned above.

In particular, F, Cl or Br represent halogen, and in the case of $Y^4$, Cl particularly preferably represents halogen. The prefix "halo" denotes one or more halogen atoms.

R preferably denotes H, $CF_2H$, $CF_3$, $CF_2CHF_2$, $CF_2CHFCl$, $CF_2CHFBr$, $CF_2CHFCF_3$, $CH_2CF_3$, $CFCl_2$, or $CF_2Cl$.

In the case of $R^1$=OH, the compound of the formula I can be present in the form of the pyridone tautomers, particularly when $R^1$ is in the 2, 4 or 6 position.

Preferred compounds of the formula I are those in which A denotes N or N→O, Z denotes O or NH, R denotes H or halogenated $(C_1-C_8)$alkyl, $R^1$, with an identical or different meaning, denotes hydrogen, halogen, amino, hydroxyl or phenylazo, which may be mono- or polysubstituted in the phenyl ring by halogen, nitro or carboxyl, or denotes a radical of the formulae $Y=C=N-$, $Y^1Y^2C=N-$ or

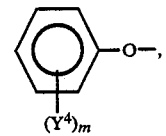

Y denotes O or S, $Y^1$ denotes halogen or $(C_1-C_3)$alkylthio, $Y^2$ denotes a radical mentioned for $Y^1$ or mercapto, $Y^4$, independently of one another, denote H, $NO_2$, $NH_2$, $-NHOH$, halogen, $-NCO$, $-NCS$, OH, $(C_1-C_6)$alkyl or $(C_1-C_6)$alkoxycarbonyl, where the two last mentioned radicals may be halogenated, and m and n, independently of one another, denote a number from 1 to 4.

Particularly preferred compounds of the formula I are those in which

A denotes N,

Z denotes O or NH,

R denotes H or halogenated $(C_1-C_4)$alkyl, $R^1$ denotes H, halogen, amino, hydroxyl or

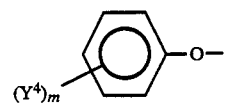

$Y^4$ denotes H, Cl, $CF_3$, $NH_2$, —NCO or ($C_1$-$C_2$)alkoxycarbonyl, which are oriented in the 2, 4 or 6 position of the phenoxy radical, and m and n denote a number from 1 to 3.

The present invention also relates to processes for the preparation of the compounds of the formula I, wherein (a) for the preparation of compounds having Z=O and R≠H, a compound of the formula (II)

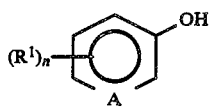
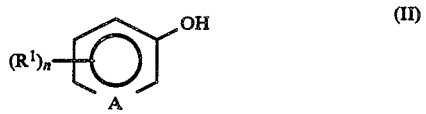

(a₁) is reacted with a compound of the formula $Y^1$—R′, in which R′ denotes the meaning of R, apart from H, and $Y^1$ denotes a nucleofugic radical, such as halogen, phenylsulfonyl, phenylsulfinyl, tosyl or mesyl, in the presence of a base, or (a₂) is reacted with a halogenated ($C_2$-$C_8$)alkene or halogenated ($C_2$-$C_8$)alkyne, in the presence of a base, or (a₃) is reacted with a halogenated carbene of the formula C(Hal)₂, where Hal, with an identical or different meaning, denotes halogen, particularly F or Cl, or (a₄) is reacted with a compound of the formula $Y^1$—CO—$R^2$, in which $R^2$ denotes halogen, halogenated ($C_1$-$C_7$)alkyl, halogenated ($C_2$-$C_7$)alkenyl or halogenated ($C_2$-$C_7$)alkynyl, and the resultant intermediate of the formula (III)

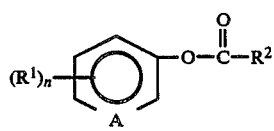

is halogenated, or (a₅) for the preparation of compounds having Z=O and R= perhalogenated ($C_1$-$C_8$)alkyl, a compound of the formula (II) is reacted with a perhalogenated ($C_1$-$C_8$)alkane in the presence of a base or in the presence of HF, or (b) for the preparation of compounds of the formula I having Z=O and R≠H, a compound of the formula (IV)

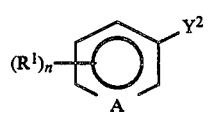

in which $Y^2$ denotes a leaving group such as halogen, nitro, diazonium, alkylsulfonyl, halogenated alkylsulfonyl, or phenylsulfonyl which may be substituted in the phenyl radical, for example, by alkyl or halogen, is reacted with an alkali metal salt of a compound of the formula OH—$CH_2$—$R^3$, in which $R^3$ has the meaning of $R^2$, apart from halogen, or (c) for the preparation of compounds of the formula I having Z=O and R=H, a compound of the formula (V),

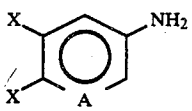

where X, independently of one another, denote halogen, is diazotized and hydrolyzed, or (d) for the preparation of compounds having Z—R=$NH_2$, a compound of the formula (VI)

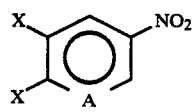

is reduced, or (e) for the preparation of compounds of the formula I which contain, in the 6 position, a phenylazo radical which is optionally substituted as mentioned above, a compound of the formula (VII)

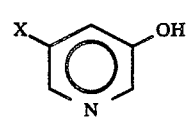

is reacted with a phenyldiazonium ion which may be substituted as specified for phenylazo of the formula (I), or (f) for the preparation of compounds having $R^1$=

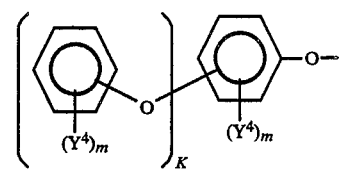

a compound of the formula (VIII)

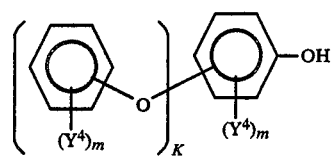

is reacted with a compound of the formula IX

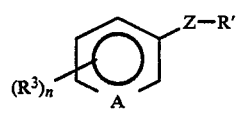

in which $R^3$ denotes a nucleofugic leaving group such as halogen, alkylsulfinyl, phenylsulfinyl, phenylsulfonyl or alkylsulfonyl, and R′ has the meaning of R, apart from hydrogen, and the products obtained under (a) to (f) are derivatized, if appropriate.

The pyridinoles of the formula II to be used as starting compounds in the preparation processes mentioned under (a) are either known, see A. Weissberger and E.

C. Taylor, The Chemistry of Heterocyclic Compounds, Pyridine and its Derivatives, Wiley, N.Y., or can be prepared according to processes (c) and (e) or by methods known to those skilled in the art.

The pyridines of the formulae IV, VI or IX to be used as starting compounds in the processes (b), (d) or (f) are known from the literature or can be prepared analogously to known processes, see A. Weissberger, E. C. Taylor loc.cit. or T. Batkowski, Rosz. Chem. 1968 (12) 2079.

The 3-pyridinoles of the formula VII to be used as starting compounds in preparation process (e) are known from the literature or can be prepared analogously to known processes, see T. Batkowski loc.cit.

(II) can be alkylated according to version ($a_1$) by reacting (II) with an alkylating reagent, such as, for example, methyl chloride, methyl bromide, methyl iodide, dimethyl sulfate, diethyl sulfate, methyl p-toluenesulfonate, methyl fluorosulfonate, methyl trifluoromethanesulfonate, ethyl methanesulfonate, 2,2,2-trifluoroethyl fluorosulfonate, 1-hydroperfluoroisopropyl fluorosulfonate, in the presence of a base, such as an alkali metal hydroxide or alkali metal carbonate. As solvent, acetone, acetonitrile, dimethylformamide, dichloromethane or dimethyl sulfoxide, for example, can be employed, optionally in the presence of phase transfer catalysts, such as TEBA or Aliquat 336. The reaction is carried out at temperatures between −100° and +200° C., preferably between 0° and 100° C., see J. March, Advanced Organic Chemistry Tokyo 1977, p. 357 ff. The compounds thus obtained are then halogenated in the side chain, if appropriate.

In process version ($a_2$), a haloalkoxy or haloalkenyloxy compound of the formula I is produced. This can be converted into other compounds of the formula I by side chain modification, for example by addition of hydrogen halide to a multiple bond, described in Houben-Weyl-Müller, Volume V/3, page 811 ff, Georg-Thieme-Verlag, Stuttgart, 1962, by addition of halogen to a multiple bond, described in Houben-Weyl-Müller, Volume V/3, p. 529 ff, by exchange of hydrogen by halogen, described in Houben-Weyl-Müller, Volume V/3, p. 564 ff, or by transhalogenation, described in Houben-Weyl-Müller, Volume V/3, p. 749 ff, 70 ff, Volume V/4, p. 354 ff, 595 ff. As base, an alkali metal hydroxide, alkali metal alcoholate, alkali metal hydride, alkali metal carbonate, alkali metal amide or trialkylamine can be employed, for example, in version ($a_2$). The reaction is carried out in a dipolar aprotic solvent such as tetrahydrofuran, dioxane, diglyme, tetraglyme, dimethoxyethane, acetonitrile, propionitrile, benzonitrile, dimethylformamide, dimethylacetamide, N-methylpyrrolidone, dimethyl sulfoxide, sulfolane, dimethyl sulfone, diphenyl sulfone, acetone, methyl ethyl ketone or hexamethylphosphoric triamide, at temperatures from −100° to +250° C., preferably −10° to +100° C. As haloalkene or haloalkyne, 1,1-difluoroethane, 1,2-difluoroethene, trifluoroethene, tetrafluoroethene, chlorotrifluoroethene, bromotrifluoroethene, iodotrifluoroethene, 1,1-dichlorodifluoroethene, trichlorofluoroethene, tetrachloroethene, hexafluoropropene, 1,1,1-trifluoropropane, 2-trifluoromethyl-1,1,1-trifluoro-2-propene, octafluoroisobutene, perfluoro-4-methyl-2-pentene, perfluoro-4-methyl-1-pentene or perfluoro-2-butyne are employed, for example.

The dihalocarbene of the formula $C(Hal)_2$ used in the halocarbene insertion according to process version ($a_3$) is generated by alpha-elimination of a trihalomethane compound, such as for example, trichloromethane, trifluoromethane, tribromomethane, triiodomethane, dichlorofluoromethane, dibromofluoromethane or bromodifluoromethane, preferably chlorodifluoromethane, using a base such as an alkali metal hydroxide, alkali metal carbonate, alkali metal alcoholate or alkali metal hydride, in solvents, such as, for example, dimethoxyethane, tetrahydrofuran, ethanol, methanol, dimethylformamide, N-methylpyrrolidone, dimethylsulfoxide or acetone, preferably 1,4-dioxane, dimethylformamide or acetonitrile, at temperatures from −100° to +200° C., preferably from 0° to 60° C. Other dihalocarbene sources may also be employed, such as salts of trihaloacetic acids, which are thermally decomposed, or trihalomethylmetal compounds, see J. March, Advanced Organic Chemistry, p. 181, 343, 496, 789, Tokyo 1977.

In process version ($a_4$), the compounds phosgene, carbonyl fluoride, trichloroacetyl chloride, dichloroacetyl chloride, chloroacetyl chloride, trichloroacetic anhydride, dichloroacetic anhydride, perchloropropionyl chloride, dichlorofluoroacetyl chloride, chlorodifluoroacetyl chloride, trifluoroacetyl chloride, trifluoroacetic anhydride, perfluoropropionyl chloride or perfluorooctanyl chloride, for example, may be used as reagents of the formula $Y^1$—CO—$R^2$. Dichloromethane, chloroform, tetrachloromethane, Frigen 113, 1,2-dichloroethane, diethyl ether, dimethoxyethane, toluene, benzene, chlorobenzene, xylene or carbondisulfide, for example, are used as solvent; if desired, organic nitrogen bases, such as triethylamine, pyridine or 4-dimethylaminopyridine, are added. The reaction can be carried out at temperatures between −20° and +50° C.

The halogenation of the compounds of the formula I thus obtained can be carried out using sulfur tetrafluoride, if appropriate in the presence of HF or phenylphosphonyl dichloride, see W. A. Sheppard, J.Org.-Chem. 29, (1964) and U.S. Pat. No. 4,419,514, CA 100, 854 125.

Process ($a_5$) can be carried out in a fashion such that the pyridinol of the formula II is reacted with a perhaloalkane, such as, for example iodotrifluoromethane, bromotrifluoromethane, chlorotrifluoromethane, dibromodifluoromethane, bromochlorodifluoromethane, tetrachloromethane, 1,2-dibromotetrafluoroethane, 1,2-dibromohexafluoropropane, iodoperfluoroethane, 2-iodoperfluoropropane, 1-iodoperfluorohexane or 1-iodoperfluorooctane, in the presence of a base, such as tetrabutylammonium hydroxide, ammonia, an alkali metal, an alkali metal hydroxide, an alkali metal hydride or an alkali metal carbonate, if desired with addition of a phase transfer catalyst, such as, for example [18]-crown-6, [15]-crown-5, TEBA (benzyltriethylammonium chloride) or Aliquat 336 (tricaprylmethylammonium chloride), in a solvent, such as, for example, benzene, toluene, dichloromethane, dimethylformamide, N-methylpyrrolidone, sulfolane, acetonitrile, tetrahydrofuran or tetraglyme, if appropriate under UV irradiation (180–350 nm), at temperatures from −50° C. to +100° C. and pressures from 0 to 100 bar. As an alternative, the pyridinol (II) can be reacted with one of the abovementioned perhaloalkanes in 500–5,000 mol % of anhydrous hydrofluoric acid, if appropriate with addition of 0.1–10 mol % of boron trifluoride, antimony pentachloride or antimony trifluoride, at temperatures from 0° to 180° C. and pressures from 0 to 100 bar, to form the pyridines of the formula I.

In addition, for the alkylation of the compounds of the formula I, a process can alternatively be used in which (II) is initially converted into its anion, an oxirane, such as, for example, hexafluoropropene oxide, octafluoroisobutene oxide, perfluoroisohex-1-ene oxide or perfluoroisohex-2-ene oxide, is subsequently added, and the carboxylate obtained is pyrolyzed, see H. Millauer et al., Angew.Chem. 97, 164 (1985).

The process according to version (b) can be carried out at temperatures between 0° and 200° C., preferably between 80° and 170° C. As alkali metal salts of the compounds of the formula $HO-CH_2R^3$, the alkali metal salts of 2,2,2-trichloroethanol, 2,2,2-trifluoroethanol, 1-hydroperfluoroisopropanol, 2,2,3,3-tetrafluoropropanol or 2,2,3,4,4,4-hexafluorobutanol, for example, can be employed. As solvent, dimethoxyethane, dimethylformamide, N-methylpyrrolidone, dimethyl sulfoxide, dimethyl sulfone, sulfolane, adipodinitrile or hexamethylphosphoric triamide, for example, preferably hexamethylphosphoric triamide, are used.

In the reaction according to version (c), the diazonium salt of (V), obtained by conventional methods, see Houben-Weyl, vol. X/3, p. 7 ff, is either heated directly in aqueous solution, see Houben-Weyl, vol. VI/1c, p. 247 ff, or hydrolyzed after its isolation, for example as the tetrafluoroborate, see Houben-Weyl, vol. X/3, p. 7 ff, or is initially acetylated and subsequently hydrolyzed, see Houben-Weyl, vol. VI/1c, p. 247 ff.

The hydrolysis is carried out in aqueous acidic solution at temperatures between $+50°$ C. and $+150°$ C., preferably between $+70°$ C. and $+120°$ C. The solvolysis in glacial acetic acid or acetic anhydride can be carried out at temperatures from $+20°$ C. to $+140°$ C., preferably between $+30°$ C. and $100°$ C. The hydrolysis of the acetate thus formed can be carried out at temperatures from $0°$ C. to $+100°$ C., preferably between $+20°$ C. and $80°$ C., in aqueous or alcoholic alkali.

For the derivatization of the compounds of the formula I thus obtained, a base-catalyzed hydrolysis, ammonolysis, a reaction with phenylhydrazines with subsequent dehydrogenation, or an N-oxidation to obtain the N-oxides of the formula I, can be carried out, see A. Weissberger and E. C. Taylor, The Chemistry of Heterocyclic Compounds, Pyridine and its Derivatives, Wiley N.Y.

The reduction of VI in process (d) can be carried out using an inorganic reducing agent (Houben-Weyl 4/1c, p. 563 ff and 4/1d,. p. 1 ff) or catalytically (Houben-Weyl, volume 4/1c, p. 482 ff).

As inorganic reducing agent, iron, which does not cause dehalogenation, is suitable, for example. The reaction is carried out in aqueous glacial acetic acid (5 to 30% by weight, preferably 15% by weight). The reaction temperature is generally between $+10°$ C. and $+120°$ C., preferably between $+20°$ and $+60°$ C.

For the catalytic hydrogenation, metal catalysts are suitable which have low activity, such as weakly active Raney nickel, noble metal sulfides, osmium/aluminum oxide, inter alia (Houben-Weyl, volume 4/1c, p. 520 ff). Lower alcohols, glycol, ethers (for example tetrahydrofuran, 1,4-dioxane, dimethoxyethane, 2-methoxyethanol), esters (for example ethyl acetate), dimethylformamide, pyridine and glacial acetic acid are suitable as solvents for the catalytic hydrogenation. The addition of bases and salts such as magnesium oxide, calcium hydroxide or sodium acetate, and DMSO likewise causes inhibition of the dehalogenation (Houben-Weyl, volume 4/1c, p. 521).

In the reaction according to version (e), the pyridinol of the formula VII is coupled to a phenyldiazonium compound, preferably in the pH range 8 to 10, in aqueous or alcoholic medium at temperatures from $-20°$ C. to $+10°$ C.

In addition, certain compounds of the formula I can be prepared by cyclization of compounds of the type

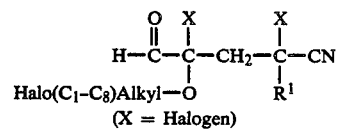

(X = Halogen)

using copper or copper salts in the presence of hydrogen halides, cf. EP-A 12,117.

In order to obtain good yields in the abovementioned process versions (a) to (e), it may sometimes be necessary, in the case $R^1=OH$ or $NH_2$, to mask the $R^1$ radical before the reaction by introduction of a protecting group; for the use of protecting groups, see T. W. Greene, Protective Groups, Wiley 1981).

The compounds of the formula I which can be obtained using processes (a) to (f) can be converted into other compounds of the formula I by known reaction steps, for example by nitration, alkylation on an amino or OH group, sulfenylation (cf. Houben-Weyl, E11, p. 110 ff), phosphorylation (cf. Houben-Weyl E2, p. 487 ff), reduction of a nitro group to an amino or —NHOH group, introduction of an amino group by exchange of halogen or another leaving group by amino (cf. Houben-Weyl, 11/1, p. 24 ff), phosgenation of an amino group, conversion of an amino group into the S=C=N— group by conventional routes (cf. Houben-Weyl, E4, p. 738 ff or p. 834 ff) or by oxidation of the pyridine to the pyridine N-oxide (A. Weissberger and E. C. Taylor, loc. cit.).

The compounds of the formula I represent valuable intermediates for the preparation of plant protection agents, see German patent application No. P 3,545,569.1, "Neue Pyridin-Derivate, Verfahren zu ihrer Herstellung, sie enthaltende Mittel und ihre Verwendung als Schädlaingsbekämpfungsmittel" [Novel pyridine derivatives, processes for the preparation thereof, agents containing same, and the use thereof as pesticides] (HOE 85/F 294) and P 3545571.3, "Heterocyclische Phenyläther, Verfahren zu ihrer Herstellung und diese enthaltende Mittel" [Heterocyclic phenyl ethers, processes for the preparation thereof, and agents containing same] (HOE 85/F 296).

For this purpose the compounds of formula I are converted, e.g., to insecticidally active benzoyl urea compounds of formula (A)

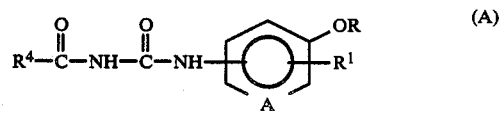

wherein $R^4$ denotes phenyl which may be substituted by halogen, $(C_1-C_3)$-alkyl, $(C_1-C_3)$-alkoxy, halo$(C_1-C_3)$-alkyl or halo$(C_1-C_3)$-alkoxy, by reacting for example a compound of formula I where $(R^1)_n$ is $Y^3NH$ with an appropriate benzoylisocyanate compound or by reacting a compound of formula I where $(R^1)_n$ is $Y=C=N—$ or $Y^1Y^2C=N—$ with a benzoylamino compound.

Alternatively the compounds of formula I may be converted to herbicidally active phenoxypyridyloxy compounds of formula B

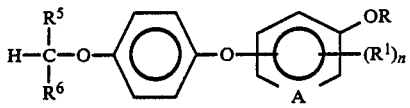

wherein $R^5$ is H or alkyl and $R^6$ is a carboxylic acid or a derivative thereof, by reacting specific compounds of formula I wherein Z is O and $R^1$ represents among other at least one leaving group such as halogen, $(C_1-C_3)$-alkylsulfonyl, phenylsulfonyl, mesyl or tosyl, with appropriate phenolic compounds.

They are furthermore suitable, in the case $R^1$=substituted phenylazo, as dyestuffs, cf. G. Schiemann, B. Cornils, Chemie und Technologie cyclischer Fluorverbindungen, [The Chemistry and Technology of Cyclic Fluorine Compounds], Ferdinand Enke-Verlag, Stuttgart (1969), p. 287-299.

In addition, the compounds of the formula (I) have surface-active actions and are suitable as impregnating agents, cf. U.S. Pat. No. 2,492,855.

The invention is described by the following examples.

CHEMICAL EXAMPLES

EXAMPLE 1

3-(2-chloro-1,1,2-trifluoroethoxy)-5,6-dichloropyridine

Chlorotrifluoroethylene was passed into a mixture of 16.4 g (0.1 mol) of 5,6-dichloro-3-pyridinol I/29 and 20 g (0.145 mol) of anhydrous potassium carbonate in 100 ml of absolute acetonitrile at 35° C. until starting material was no longer present. The solid was filtered off under suction, the solvent was removed by distillation, and the residue was taken up in ether and washed until neutral. After drying over MgSO$_4$ and removal of the ether by distillation, the residue was distilled in a high vacuum.

Yield 83% Boiling point 85° C./0.03 mbar

EXAMPLE 2

3-(1,1,2,3,3,3-hexafluoro-1-propyloxy)-2-hydroxypyridine 2.6 g (10 mmol) of 2-amino-3-(1,1,2,3,3,3-hexafluoro-1propyloxy)pyridine were diazotized at 0° C. in 35 ml of 2N sulfuric acid using 0.76 g (11 mmol) of sodium nitrite in 5 ml of water. The reaction mixture was stirred for 30 minutes and the product was extracted using ethyl acetate. The organic phase was washed until neutral, dried using MgSO$_4$ and concentrated by evaporation.

Yield 75% Melting point 89° C.

EXAMPLE 3

5,6-dichloro-3-difluoromethoxypyridine

Chlorodifluoromethane was passed at 50° C. into a mixture of 32.8 g (0.2 mol) of 5,6-dichloro-3-pyridinol in 200 ml of 1,4-dioxane and 40 g (1 mol) of sodium hydroxide in 100 ml of water until starting material was no longer present. The further procedure was then carried out as described in Example 1.

Yield 77% Boiling point 57°-60° C./0.1 mbar

EXAMPLE 4

2-chloro-5-(1,1,2,2-tetrafluoroethoxy)pyridine 14.9 g (97 mmol) of phosphoroxy chloride were added to a mixture of 13.6 g (65 mmol) of 5-(1,1,2,2-tetrafluoroethoxy)-2-hydroxypyridine and 5.6 g (43 mmol) of quinoline, and stirred for 3 hours at 120° C. The mixture was poured at 20° C. onto ice, extracted with dichloromethane and dried over sodium sulfate. The solvent was evaporated on a rotary evaporator and the residue was distilled at 6 mbar.

Yield 11.7 g (79%) Boiling point 79° C./6 mbar

EXAMPLE 5

2-chloro-5-(2-chloro-1,1,2-trifluoroethoxy)pyridine

A solution of 7.59 g (0.11 mol) of sodium nitrite in 15 ml of water was added dropwise with stirring to a solution of 22.6 g (0.1 mol) of 2-amino-5-(2-chloro-1,1,2-trifluoroethoxy)pyridine in 100 ml of concentrated HCl at 0° C. The mixture was stirred for one hour at 50° C., the pH was adjusted to 6.5 using 2N KOH, and the product was extracted three times with 100 ml of dichloromethane in each case. After drying over sodium sulfate and removal of the solvent by evaporation on a rotary evaporator, the residue was distilled at 6.5 mbar and 13 g of 2-chloro-5-(2-chloro-1,1,2-trifluoroethoxy)pyridine were obtained as a colorless liquid.

Yield 53% Boiling point: 101° C./6.5 mbar

EXAMPLE 6

5-(1,1,2,2-tetrafluoroethoxy)-2-hydroxypyridine

A solution of 10.3 g (149 mmol) of sodium nitrite in 16.5 ml of water was added dropwise with stirring to a solution of 23 g (109 mmol) of 2-amino-5-(1,1,2,2-tetrafluoroethoxy)pyridine in 103 ml of water and 21.9 g of concentrated sulfuric acid at 0° C. The mixture was stirred for 3 hours at 20°-25° C., and the colorless solid was filtered off under suction and washed with water until free of acid.

Yield 16.4 g (71%) Melting point 103° C.

EXAMPLE 7

2-amino-5-(2-chloro-1,1,2-trifluoroethoxy)pyridine

In a 1 liter VA stainless steel autoclave, 85.1 g (0.24 mol) of 5-(2-chloro-1,1,2-trifluoroethoxy)-2-(4-nitrophenylazo)pyridine were hydrogenated in 600 ml of acetic acid, with addition of 10 g of palladium (10%) on activated charcoal, using 61 bar (take-up) of hydrogen at 20°-25° C. The mixture was filtered and the solvent removed by distillation on a rotary evaporator. The residue was taken up in 500 ml of dichloromethane, washed with 100 ml of 20% strength aqueous sodium carbonate and four times with 100 ml of water in each case, and dried over sodium sulfate. The solvent was subsequently removed by evaporation on a rotary evaporator and the residue was distilled in a high vacuum.

Yield 54% Melting point 63° C. nacreously shiny leaflets

EXAMPLE 8

3-chloro-5-(2-chloro-1,1,2-trifluoroethoxy)-2-hydroxypyridine (a) 23.6 g (104 mmol) of 5-(2-chloro-1,1,2-trifluoroethoxy)2-hydroxypyridine were dissolved in 80 ml of concentrated HCl, and a solution of 5.3 g (42 mmol) of potassium chlorate in 60 ml of water was added dropwise with stirring. The mixture was stirred for 1 hour at 50°-60° C., and the solid was filtered off at 0° C. and washed with ice-water until free of acid. After crystallization from methanol/water, 20.3 g of colorless crystals were obtained.

Yield 75% Melting point 140° C.

(b) 2.2 liters of chlorotrifluoroethylene were introduced from a gas burette into a gas-tight stirred apparatus containing a mixture of 11.1 g (0.1 mol) of 2 5-dihydroxypyridine, and 13.8 g (0.1 mol) of potassium carbonate and 100 ml of dry dimethylformamide, with stirring at 75° C. The mixture was filtered through Celite at 20°-25° C. and the solvent was removed by evaporation in vacuo. The residue was dissolved in 25 ml of concentrated hydrochloric acid, and a solution of 4.3 g (35 mmol) of potassium chlorate in 60 ml of $H_2O$ was added dropwise to this solution with stirring at 60° C. After stirring for 0.5 hour at 60° C., the pH was adjusted to 6.5 at 20°-25° C. using 2N KOH, and the organic components were extracted four times with 100 ml of ethyl acetate in each case. 6.0 g of product were isolated by flash chromatography as a fraction having the $R_f$ value of 0.91 (dichloromethane/silica gel).

Yield 23% over two stages Melting point 140° C.

EXAMPLE 9

5-(2-chloro-1,1,2-trifluoroethoxy)-2-(4-nitrophenylazo)-pyridine 26 liters of chlorotrifluoroethene were introduced from a gas burette into a gas-tight stirred apparatus containing a mixture of 244 g (1.0 mol) of 5-hydroxy-2-(4-nitrophenylazo)pyridine, 138 g (1.0 mol) of potassium carbonate and 2 liters of dry DMF. The mixture was filtered through Celite, and the solid was washed with 1 liter of acetone. The solvent was removed from the filtrate by evaporation on a rotary evaporator. The residue was taken up in 2.5 liters of ethyl acetate and washed four times with 500 ml of saturated sodium chloride solution in each case.

After drying over potassium carbonate, the solvent was concentrated by evaporation. Purification was effected by flash distillation in a high vacuum.

Yield 234 g (65%) of red crystals Melting point: 107° C.

EXAMPLE 10

3-amino-5,6-dichloropyridine 77.2 g (0.4 mol) of 2,3-dichloro-5-nitropyridine were dissolved in 135 ml of glacial acetic acid, and 800 ml of water were added with stirring. 111.7 g (2 mol) of iron powder were introduced in portions into the mixture (temperature $\leq 50°$ C.). After completion of the reaction, the mixture is filtered under suction and the product extracted using ethyl acetate. The organic phase was washed with water until neutral, dried using $MgSO_4$ and concentrated by evaporation. The product was recrystallized from toluene.

Yield 85% Melting point 107° C.

EXAMPLE 11

5,6-dichloro-3-pyridinol

Process (a)

8.15 g (50 mmol) of 3-amino-5,6-dichloropyridine were dissolved in 100 ml of 8N $H_2SO_4$ and diazotized at 0° C. using 3.55 g (53 mmol) of sodium nitrite in 9 ml of water. The cold diazonium salt solution was added dropwise to 100° C. warm 60% strength sulfuric acid.

After completion of the nitrogen elimination, the mixture was neutralized and extractively distilled using toluene. The dried toluene phase was concentrated by evaporation and the residue was recrystallized repeatedly from toluene.

Melting point 184°-185° C.

Process (b)

7.8 g (0.6 mol) of 3-amino-5,6-dichloropyridine were dissolved in 900 ml of 50% strength $HBF_4$ and diazotized at 0° C. using 43.5 g (0.63 mol) of sodium nitrite in 600 ml of water. The mixture was stirred for 0.5 hours, and the diazonium salt was filtered off under suction and washed with ice-water and ether. The dried salt was then warmed slowly to 70° C. in 600 ml of acetic anhydride. When the $N_2$ evolution was complete, the mixture was concentrated on a rotary evaporator, and the residue was taken up in ether, washed with water until neutral, dried using $MgSO_4$, concentrated by evaporation and distilled in vacuo. 3-acetoxy-5,6-dichloropyridine of boiling point 102°-103° C. 0.01 mbar was obtained.

41.2 g (0.2 mol) of 3-acetoxy-5,6-dichloropyridine in 20 ml of methanol were added dropwise at room temperature to 300 ml of methanolic KOH (2N) and stirred for 30 minutes. When the reaction was complete, the reaction mixture was concentrated by evaporation, and 50 ml of water were added to the residue and neutralized using glacial acetic acid; the product was filtered off under suction, washed with water and dried. After recrystallization from toluene, the product having a yield of 95% and a melting point of 184°-185° C. was obtained.

For simplification, the two separate process steps described in process (b) for compound 29 can also be carried out as a "one-pot process",

EXAMPLE 12

5,6-dichloro-3-pyridinol-1-oxide 3.28 g (20 mmol) of 5,6-dichloro-3-pyridinol in 15 ml of glacial acetic acid were N-oxidized at 100° C. using 2.14 g (21 mmol) of 35% hydrogen peroxide. When the reaction was complete, the mixture was neutralized, extracted with ethyl acetate and washed until neutral, and the solvent was removed by evaporation.

Yield 85% Melting point 174°-175° C.

EXAMPLE 13

3-chloro-5-hydroxy-2-(4-nitrophenylazo)pyridine 27.6 g (0.2 mol) of 4-nitroaniline were dissolved in a mixture of 60 ml of concentrated HCl and 500 ml of water by stirring for one hour at 30° C. After addition of 700 g of ice, a solution of 14.6 g (0.21 mol) of sodium nitrite in 140 ml of water was added dropwise at a maximum of 4° C. 2.6 g of activated charcoal and 5 g of silica gel were added at 0° C., and the mixture was filtered. At pH 8-8.5, set by continuous metered addition of 2N KOH, the solution obtained was added dropwise at 0° C. with stirring to a solution of 25.9 g (0.2 mol) of 5-chloro-3-hydroxypyridine and 11.2 g of KOH in 500 ml of $H_2O$. When the addition was complete, the mixture was stirred for 1 hour at 0° C. and 50 ml of acetic acid were added, and the azo compound was thus obtained in the form of red crystals.

Yield 52.7 g (94%) Melting point: 207° C.

EXAMPLE 14

5-amino-3-chloro-2-(2,6-dichlorophenoxy)pyridine 6.39 g (20 mmol) of 3-chloro-2-(2,6-dichlorophenoxy)-5nitropyridine were suspended in 7 ml of glacial acetic acid and 40 ml of water, and 5.6 g (0.1 mol) of iron powder were added in portions at room temperature (temperature 50° C.). The mixture was stirred for 1 hour, complete conversion determined by means of TLC, the mixture was filtered through a glass filter frit under suction, and the filter cake was carefully washed with ethyl acetate. The organic phase was washed with water until neutral, dried using MgSO$_4$ and concentrated by evaporation.

EXAMPLE 15

4-(3-chloro-5-difluoromethoxy-2-pyridyloxy)-3,5-dichloroaniline 9.26 g (52 mmol) of 3,5-dichloro-4-hydroxyaniline, 10.1 g (50 mmol) of 2,3-dichloro-5-difluoromethoxypyridine and 10.4 g of anhydrous potassium carbonate were stirred for 15 hours at 105° C. under argon in 50 ml of anhydrous dimethyl sulfoxide. The dimethyl sulfoxide was then removed by distillation, and the residue was taken up in 100 ml of ether, washed twice with 30 ml of 5% strength potassium carbonate solution and with water until neutral and concentrated by evaporation.

Yield 14.8 g (83%) Crude product, dark oil

EXAMPLE 16

4-(3-chloro-5-difluoromethoxy-2-pyridyloxy)-3,5-dichlorophenyl isocyanate 2 g (5.8 mmol) of 4-(3-chloro-5-difluoromethoxy-2-pyridyloxy)-3,5-dichloroaniline were dissolved in 25 ml of anhydrous toluene, 2.9 g (29 mmol) of phosgene gas were introduced at 0° C., and the mixture was slowly warmed to 105° C. Excess phosgene was expelled using inert gas, the solvent was concentrated by evaporation, and the residue was dried in a high vacuum.

Yield 2.1 g (quantitative); red-brown oil IR 2200 cm$^{-1}$ (N=C=O)

The compounds collated in the following table can be synthesized according to the abovementioned preparation methods.

TABLE 1

Pyridines of the formula

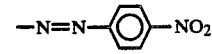

I

| Example | Z | X$^1$ | X$^2$ | X$^3$ | X$^4$ | —R | A | m.p. °C. b.p. °C./mbar |
|---|---|---|---|---|---|---|---|---|
| 17 | O | Cl | H | Cl | Cl | —CF$_2$CHClF | N | |
| 18 | O | H | H | Cl | Cl | —CClF$_2$ | N | 95/0.01 |
| 19 | O | Cl | H | Cl | Cl | —CClF$_2$ | N | 97/0.01 |
| 20 | O | H | H | Cl | Cl | —CF$_2$CHFCF$_3$ | N | 100/0.02 |
| 21 | O | I | H | H | H | —CF$_2$CHClF | N | 69/0.01 |
| 22 | O | Br | H | Cl | H | —CF$_2$CHClF | N | 64/0.001 |
| 23 | O | Br | H | Cl | Br | —CF$_2$CHClF | N | 97/0.001 |
| 24 | O | Br | H | H | Br | —CF$_2$CHClF | N | 105/0.001 |
| 25 | O | H | H | Cl | H | —CF$_2$CHFCF$_3$ | N | 40/0.04 |
| 26 | O | H | H | H | H | —CF$_2$CHFCF$_3$ | N→O | 42–44 |
| 27 | O | NH$_2$ | H | H | H | —CF$_2$CHFCF$_3$ | N | 40–41 |
| 28 | O | H | H | H | H | —F$_2$CHClF | N | 84/10 |
| 29 | O | H | H | H | Cl | —CF$_2$CHFCF$_3$ | N | 88/6 |
| 30 | O | H | H | H | OH | —CF$_2$CHClF | N | 85 |
| 31 | O | H | H | H | NH$_2$ | —CF$_2$CHF$_2$ | N | 60–70/0.01 |
| 32 | O | H | H | Cl | Cl | —CF$_2$CHF$_2$ | N | 60–61/0.005 |
| 33 | O | H | H | H | —N=N—C$_6$H$_4$—NO$_2$ | —CF$_2$CHF$_2$ | N | 122–125 |
| 34 | O | H | H | H | —N=N—C$_6$H$_4$—NO$_2$ | —CF$_2$CHFCF$_3$ | N | 106 |
| 35 | O | H | H | H | —N=N—C$_6$H$_4$—NO$_2$ | —CHF$_2$ | N | 103–105 |
| 36 | O | H | H | H | NH$_2$ | —CF$_2$CHFCF$_3$ | N | 74/0.1 |
| 37 | O | H | H | H | NH$_2$ | —CHF$_2$ | N | 62–65/0.1 |
| 38 | O | H | H | Br | NH$_2$ | —CF$_2$CHFCl | N | 85/0.1 |
| 39 | O | H | H | Br | NH$_2$ | CF$_2$CHFCF$_3$ | N | 72–73/0.1 |
| 40 | O | H | H | Cl | NH$_2$ | CFCHF$_2$ | N | 70–72/0.1 |
| 41 | O | —N=N—C$_6$H$_4$—NO$_2$ | H | Cl | H | OCF$_2$H | N | 153–157 |
| 42 | NH | H | H | F | F | H | N | |
| 43 | NH | H | H | F | Cl | H | N | |
| 44 | NH | H | H | F | Br | H | N | |

TABLE 1-continued

Pyridines of the formula I $$\begin{array}{c} X^2 \\ X^3 \diagdown \diagup Z-R \\ \diagup A \diagdown \\ X^4 \quad X^1 \end{array}$$

| Example | Z | $X^1$ | $X^2$ | $X^3$ | $X^4$ | —R | A | m.p. °C. b.p. °C./mbar |
|---|---|---|---|---|---|---|---|---|
| 45 | NH | H | H | Cl | F | H | N | |
| 46 | NH | H | H | Cl | Br | H | N | 104 |
| 47 | NH | H | H | Br | F | H | N | |
| 48 | NH | H | H | Br | Cl | H | N | 113 |
| 49 | NH | H | H | Br | Br | H | N | |
| 50 | O | H | H | F | F | H | N | |
| 51 | O | H | H | F | Cl | H | N | |
| 52 | O | H | H | F | Br | H | N | |
| 53 | O | H | H | Cl | F | H | N | |
| 54 | O | H | H | Cl | Br | H | N | 185 |
| 55 | O | H | H | Br | F | H | N | |
| 56 | O | H | H | Br | Cl | H | N | 178 |
| 57 | O | H | H | Br | Br | H | N | |
| 58 | O | Br | H | Cl | Br | H | N | 180 |
| 59 | O | Br | H | F | Br | H | N | |
| 60 | O | Br | H | Br | Br | H | N | |
| 61 | O | Cl | Cl | Cl | Cl | H | N | |
| 62 | O | H | H | Br | $O_2N-\phenyl-N=N-$ | H | N | |
| 63 | O | H | H | F | $O_2N-\phenyl-N=N-$ | H | N | |
| 64 | O | H | H | F | F | H | N→O |
| 65 | O | H | H | F | Cl | H | " | |
| 66 | O | H | H | F | Br | H | " | |
| 67 | O | H | H | Cl | F | H | " | |
| 68 | O | H | H | Cl | Br | H | " | |
| 69 | O | H | H | Br | F | H | " | |
| 70 | O | H | H | Br | Cl | H | " | |
| 71 | O | H | H | Br | Br | H | " | |
| 72 | O | H | H | F | F | $CH_3CO$ | N | |
| 73 | O | H | H | F | Cl | $CH_3CO$ | N | |
| 74 | O | H | H | F | Br | $CH_3CO$ | N | |
| 75 | O | H | H | Cl | F | $CH_3CO$ | N | |
| 76 | O | H | H | Cl | Cl | $CH_3CO$ | N | 102-3/0.01 |
| 77 | O | H | H | Cl | Br | $CH_3CO$ | N | 103-8/0.01 |
| 78 | O | H | H | Br | F | $CH_3CO$ | N | |
| 79 | O | H | H | Br | Cl | $CH_3CO$ | N | 103/0.01 |
| 80 | O | H | H | Br | Br | $CH_3CO$ | N | |
| 81 | O | H | H | F | F | $CH_3CO$ | N→O |
| 82 | O | H | H | F | Cl | $CH_3CO$ | " | |
| 83 | O | H | H | F | Br | $CH_3CO$ | " | |
| 84 | O | H | H | Cl | F | $CH_3CO$ | " | |
| 85 | O | H | H | Cl | Cl | $CH_3CO$ | " | |
| 86 | O | H | H | Cl | Br | $CH_3CO$ | " | |
| 87 | O | H | H | Br | F | $CH_3CO$ | " | |
| 88 | O | H | H | Br | Cl | $CH_3CO$ | " | |
| 89 | O | H | H | Br | Br | $CH_3CO$ | " | |
| 90 | O | H | H | H | H | $CHF_2$ | N | 114/80 |
| 91 | O | H | H | H | H | $CF_2Cl$ | N | |
| 92 | O | H | H | H | H | $CF_3$ | N | |
| 93 | O | H | H | H | H | $CF_2CHF_2$ | N | |
| 94 | O | H | H | H | H | $CF_2CHFBr$ | N | |
| 95 | O | H | H | H | H | $CH_2CF_3$ | N | |
| 96 | O | H | H | H | H | $CF_2CHFCF_3$ | N | |
| 97 | O | H | H | H | H | $CHF_2$ | N→O |
| 98 | O | H | H | H | H | $CF_2Cl$ | " | |
| 99 | O | H | H | H | H | $CF_3$ | " | |
| 100 | O | H | H | H | H | $CF_2CHF_2$ | " | |
| 101 | O | H | H | H | H | $CF_2CHFCl$ | " | |
| 102 | O | H | H | H | H | $CF_2CHFBr$ | " | |
| 103 | O | H | H | H | F | $CF_2H$ | N | 60/18 |
| 104 | O | H | H | H | F | $CF_2Cl$ | N | |
| 105 | O | H | H | H | F | $CF_3$ | N | |
| 106 | O | H | H | H | F | $CF_2CHF_2$ | N | |

TABLE 1-continued

Pyridines of the formula I

| Example | Z | $X^1$ | $X^2$ | $X^3$ | $X^4$ | —R | A | m.p. °C. b.p. °C./mbar |
|---|---|---|---|---|---|---|---|---|
| 107 | O | H | H | H | F | $CF_2CHFCl$ | N | oil |
| 108 | O | H | H | H | F | $CF_2CHFBr$ | N | |
| 109 | O | H | H | H | F | $CH_2CF_3$ | N | |
| 110 | O | H | H | H | F | $CF_2CHFCF_3$ | N | |
| 111 | O | H | H | H | Cl | $CHF_2$ | N | |
| 112 | O | H | H | H | Cl | $CF_2Cl$ | N | |
| 113 | O | H | H | H | Cl | $CF_3$ | N | |
| 114 | O | H | H | H | Cl | $CH_2CF_3$ | N | |
| 115 | O | H | H | H | Br | $CF_2H$ | N | |
| 116 | O | H | H | H | Br | $CF_2Cl$ | N | |
| 117 | O | H | H | H | Br | $CF_3$ | N | |
| 118 | O | H | H | H | Br | $CF_2CHF_2$ | N | |
| 119 | O | H | H | H | Br | $CF_2CHFCl$ | N | |
| 120 | O | H | H | H | Br | $CF_2CHFBr$ | N | |
| 121 | O | H | H | H | Br | $CH_2CF_3$ | N | |
| 122 | O | H | H | H | Br | $CF_2CHFCF_3$ | N | |
| 123 | O | H | H | H | Cl | $CF_2H$ | N→O | |
| 124 | O | H | H | H | Cl | $CF_2Cl$ | " | |
| 125 | O | H | H | H | Cl | $CF_3$ | " | |
| 126 | O | H | H | H | F | $CF_2CHF_2$ | " | |
| 127 | O | H | H | H | F | $CF_2CHFCl$ | " | |
| 128 | O | H | H | H | Cl | $CF_2CHFBr$ | " | |
| 129 | O | H | H | H | Cl | $CH_2CF_3$ | " | |
| 130 | O | H | H | H | Br | $CF_2CHFCF_3$ | " | |
| 131 | O | Br | H | H | H | $CF_2CHFCl$ | N | 85–95/0.08 |
| 132 | O | Br | H | Cl | H | $CHF_2$ | N | 46–8/0.01 |
| 133 | O | H | H | Cl | H | $CHF_2$ | N | 32/0.01 |
| 134 | O | H | H | F | F | $CHF_2$ | N | |
| 135 | O | H | H | F | F | $CF_2Cl$ | N | |
| 136 | O | H | H | F | F | $CF_3$ | N | |
| 137 | O | H | H | F | F | $CF_2CHF_2$ | N | |
| 138 | O | H | H | F | F | $CF_2CHFCl$ | N | |
| 139 | O | H | H | F | F | $CF_2CHFBr$ | N | |
| 140 | O | H | H | F | F | $CH_2CF_3$ | N | |
| 141 | O | H | H | F | F | $CF_2CHFCF_3$ | N | |
| 142 | O | H | H | F | Cl | $CHF_2$ | N | |
| 143 | O | H | H | F | Cl | $CF_2Cl$ | N | |
| 144 | O | H | H | F | Cl | $CF_3$ | N | |
| 145 | O | H | H | F | Cl | $CF_2CHF_2$ | N | |
| 146 | O | H | H | F | Cl | $CF_2CHClF$ | N | |
| 147 | O | H | H | F | Cl | $CF_2CHFBr$ | N | |
| 148 | O | H | H | F | Cl | $CH_2CF_3$ | N | |
| 149 | O | H | H | F | Cl | $CF_2CHFCF_3$ | N | |
| 150 | O | H | H | F | Br | $CHF_2$ | N | |
| 151 | O | H | H | F | Br | $CF_2Cl$ | N | |
| 152 | O | H | H | F | Br | $CF_3$ | N | |
| 153 | O | H | H | F | Br | $CF_2CHF_2$ | N | |
| 154 | O | H | H | F | Br | $CF_2CHFCl$ | N | |
| 155 | O | H | H | F | Br | $CF_2CHFBr$ | N | |
| 156 | O | H | H | F | Br | $CH_2CF_3$ | N | |
| 157 | O | H | H | F | Br | $CF_2CHFCF_3$ | N | |
| 158 | O | H | H | Cl | F | $CHF_2$ | N | |
| 159 | O | H | H | Cl | F | $CF_2Cl$ | N | |
| 160 | O | H | H | Cl | F | $CF_3$ | N | |
| 161 | O | H | H | Cl | F | $CF_2CHF_2$ | N | |
| 162 | O | H | H | Cl | F | $CF_2CHFCl$ | N | |
| 163 | O | H | H | Cl | F | $CF_2CHFBr$ | N | |
| 164 | O | H | H | Cl | F | $CH_2CF_3$ | N | |
| 165 | O | H | H | Cl | F | $CF_2CHFCF_3$ | N | |
| 166 | O | H | H | Cl | Cl | $CF_3$ | N | 66–7/15 |
| 167 | O | H | H | Cl | Cl | $CF_2CHFBr$ | N | |
| 168 | O | H | H | Cl | Cl | $CH_2CF_3$ | N | |
| 169 | O | H | H | Cl | Br | $CHF_2$ | N | 68–70/0.1 |
| 170 | O | H | H | Cl | Br | $CF_2Cl$ | N | |
| 171 | O | H | H | Cl | Br | $CF_3$ | N | |
| 172 | O | H | H | Cl | Br | $CF_2CHF_2$ | N | |
| 173 | O | H | H | Cl | Br | $CF_2CHFCl$ | N | |
| 174 | O | H | H | Cl | Br | $CF_2CHFBr$ | N | |
| 175 | O | H | H | Cl | Br | $CH_2CF_3$ | N | |
| 176 | O | H | H | Cl | Br | $CF_2CHFCF_3$ | N | |
| 177 | O | H | H | Br | F | $CHF_2$ | N | |

TABLE 1-continued

Pyridines of the formula I $$\begin{array}{c} X^2 \\ X^3 \diagup \diagdown Z-R \\ \| \quad \| \\ X^4 \diagdown \diagup X^1 \\ A \end{array}$$

| Example | Z | $X^1$ | $X^2$ | $X^3$ | $X^4$ | —R | A | m.p. °C. b.p. °C./mbar |
|---|---|---|---|---|---|---|---|---|
| 178 | O | H | H | Br | F | $CF_2Cl$ | N | |
| 179 | O | H | H | Br | F | $CF_3$ | N | |
| 180 | O | H | H | Br | F | $CF_2CHF_2$ | N | |
| 181 | O | H | H | Br | F | $CF_2CHFCl$ | N | |
| 182 | O | H | H | Br | F | $CF_2CHFBr$ | N | |
| 183 | O | H | H | Br | F | $CH_2CF_3$ | N | |
| 184 | O | H | H | Br | F | $CF_2CHFCF_3$ | N | |
| 185 | O | H | H | Br | Cl | $CF_2H$ | N | 100/0.01 |
| 186 | O | H | H | Br | Cl | $CF_2Cl$ | N | |
| 187 | O | H | H | Br | Cl | $CF_3$ | N | |
| 188 | O | H | H | Br | Cl | $CF_2CHF_2$ | N | |
| 189 | O | H | H | Br | Cl | $CF_2CHFCl$ | N | 123/24 |
| 190 | O | H | H | Br | Cl | $CF_2CHFBr$ | N | 123/24 |
| 191 | O | H | H | Br | Cl | $CH_2CF_3$ | N | |
| 192 | O | H | H | Br | Cl | $CF_2CHFCF_3$ | N | |
| 193 | O | H | H | Br | Br | $CHF_2$ | N | |
| 194 | O | H | H | Br | Br | $CF_2Cl$ | N | |
| 195 | O | H | H | Br | Br | $CF_3$ | N | |
| 196 | O | H | H | Br | Br | $CF_2CHF_2$ | N | |
| 197 | O | H | H | Br | Br | $CF_2CHFCl$ | N | |
| 198 | O | H | H | Br | Br | $CF_2CHFBr$ | N | |
| 199 | O | H | H | Br | Br | $CH_2CF_3$ | N | |
| 200 | O | H | H | Br | Br | $CF_2CHFCF_3$ | N | |
| 201 | O | H | H | Cl | Cl | $CH_2C{\equiv}CCl$ | N | |
| 202 | O | H | H | Br | F | $CH_2{-}CCl{=}CHCl$ | N | |
| 203 | O | H | H | Cl | Br | $CH_2{-}CH{=}CHCl$ | N | |
| 204 | O | Br | H | H | Br | $CF_2CHFCF_3$ | N | 135-7/18 |
| 205 | O | H | H | F | F | $CHF_2$ | N→O | |
| 206 | O | H | H | Cl | F | $CF_2Cl$ | N→O | |
| 207 | O | H | H | Br | F | $CF_3$ | N→O | |
| 208 | O | H | H | F | Cl | $CF_2CHF_2$ | N→O | |
| 209 | O | H | H | Cl | Cl | $CF_2CHFCl$ | N→O | 80-3/0.0001 |
| 210 | O | H | H | Br | Cl | $CF_2CHFBr$ | N→O | |
| 211 | O | H | H | Cl | H | $CF_2CHFCl$ | N→O | 100-101/0.01 |
| 212 | O | H | H | Br | Br | $CF_2CHFCF_3$ | N→O | |
| 213 | O | H | H | H | $NH_2$ | $CF_2Cl$ | N | |
| 214 | O | H | H | H | $NH_2$ | $CF_3$ | N | |
| 215 | O | H | H | H | $NH_2$ | $CF_2CHBrF$ | N | |
| 216 | O | H | H | H | $NH_2$ | $CH_2CF_3$ | N | |
| 217 | O | H | H | Cl | $NH_2$ | $CF_2H$ | N | 60/0.05 |
| 218 | O | H | H | Cl | $NH_2$ | $CF_2Cl$ | N | |
| 219 | O | H | H | Cl | $NH_2$ | $CF_3$ | N | |
| 220 | O | H | H | Cl | $NH_2$ | $CF_2CHFCl$ | N | |
| 221 | O | H | H | Cl | $NH_2$ | $CF_2CHFBr$ | N | |
| 222 | O | H | H | Cl | $NH_2$ | $CH_2CF_3$ | N | |
| 223 | O | H | H | Cl | $NH_2$ | $CF_2CHFCF_3$ | N | |
| 224 | O | H | H | Br | $NH_2$ | $CHF_2$ | N | |
| 225 | O | H | H | Br | $NH_2$ | $CF_2Cl$ | N | |
| 226 | O | H | H | Br | $NH_2$ | $CF_3$ | N | |
| 227 | O | H | H | Br | $NH_2$ | $CF_2CHF_2$ | N | |
| 228 | O | H | H | Br | $NH_2$ | $CF_2CHFBr$ | N | |
| 229 | O | H | H | Br | $NH_2$ | $CH_2CF_3$ | N | |
| 230 | O | H | H | Br | $NH_2$ | $CF_3$ | N | |
| 231 | O | $NH_2$ | H | H | H | $CHF_2$ | N | 50/0.3 |
| 232 | O | H | H | H | OH | $CHF_2$ | N | 99-102 |
| 233 | O | H | H | H | OH | $CF_2Cl$ | N | |
| 234 | O | H | H | H | OH | $CF_3$ | N | |
| 235 | O | H | H | H | OH | $CF_2CHFBr$ | N | |
| 236 | O | H | H | H | OH | $CH_2CF_3$ | N | |
| 237 | O | H | H | H | OH | $CF_2CHFCF_3$ | N | 79-84 |
| 238 | O | H | H | Cl | OH | $CHF_2$ | N | 140-143 |
| 239 | O | H | H | Cl | OH | $CF_2Cl$ | N | |
| 240 | O | H | H | Cl | OH | $CF_3$ | N | |
| 241 | O | H | H | Cl | OH | $CF_2CHF_2$ | N | 150-3 |

TABLE 1-continued

Pyridines of the formula with substituents $X^2$, $X^3$ on one side, $Z-R$, and $X^4$, $X^1$ on the A ring.

| Example | Z | $X^1$ | $X^2$ | $X^3$ | $X^4$ | —R | A | m.p. °C. b.p. °C./mbar |
|---------|---|-------|-------|-------|-------|-----|---|------------------------|
| 242 | O | H | H | Cl | OH | $CF_2CHFBr$ | N | |
| 243 | O | H | H | Cl | OH | $CH_2CF_3$ | N | |
| 244 | O | H | H | Cl | OH | $CF_2CHFCF_3$ | N | 113–4 |
| 245 | O | H | H | Br | OH | $CHF_2$ | N | |
| 246 | O | H | H | Br | OH | $CF_2Cl$ | N | |
| 247 | O | H | H | Br | OH | $CF_3$ | N | |
| 248 | O | H | H | Br | OH | $CF_2CHF_2$ | N | |
| 249 | O | H | H | Br | OH | $CF_2CHFCl$ | N | oil |
| 250 | O | H | H | Br | OH | $CF_2CHFBr$ | N | |
| 251 | O | H | H | Br | OH | $CH_2CF_3$ | N | |
| 252 | O | H | H | Br | OH | $CF_2CHFCF_3$ | N | |
| 253 | O | H | H | H | $HO_2C$-C$_6H_4$-N=N— | $CF_2CHFCl$ | N | oil |
| 254 | O | H | H | Cl | $O_2N$-C$_6H_4$-N=N— | $CHF_2$ | N | oil |
| 255 | O | H | H | H | $H_2N$-(2,6-diCl-C$_6H_2$)-O— | $CHF_2$ | N | |
| 256 | O | H | H | H | $H_2N$-(2,6-diCl-C$_6H_2$)-O— | $CF_2Cl$ | N | |
| 257 | O | H | H | H | " | $CF_3$ | N | |
| 258 | O | H | H | H | " | $CF_2CHF_2$ | N | |
| 259 | O | H | H | H | " | $CF_2CHFCl$ | N | oil ($n_D^{20}$ 1.5865) |
| 260 | O | H | H | H | " | $CF_2CHFBr$ | N | |
| 261 | O | H | H | H | " | $CH_2CF_3$ | N | |
| 262 | O | H | H | H | " | $CF_2CHFCF_3$ | N | |
| 263 | O | H | H | F | " | $CHF_2$ | N | |
| 264 | O | H | H | Cl | " | $CF_2Cl$ | N | 98–99 |
| 265 | O | H | H | Cl | " | $CF_3$ | N | 83–5 |
| 266 | O | H | H | Cl | " | $CF_2CHF_2$ | N | oil ($n_D^{20}$ 1.5415) |
| 267 | O | H | H | Cl | " | $CF_2CHFCl$ | N | oil ($n_D^{20}$ 1.5963) |
| 268 | O | H | H | F | " | $CF_2CHFBr$ | N | |
| 269 | O | H | H | Br | " | $CH_2CF_3$ | N | |
| 270 | O | H | H | Cl | " | $CF_2CHFCF_3$ | N | oil ($n_D^{20}$ 1.5873) |
| 271 | O | H | H | Br | " | $CF_2CHFCl$ | N | oil ($n_D^{20}$ 1.5921) |
| 272 | O | H | H | Br | " | $CHF_2$ | N | oil ($n_D^{20}$ 1.5798) |
| 273 | O | $H_2N$-(2,6-diCl-C$_6H_2$)-O— | H | Cl | H | $CHF_2$ | N | oil ($n_D^{20}$ 1.5908) |
| 274 | O | $H_2N$-(2,6-diCl-C$_6H_2$)-O— | H | Cl | H | $CF_2CHFCl$ | N | oil ($n_D^{20}$ 1.5763) |
| 275 | O | H | H | F | $H_2N$-(2,6-diCl-C$_6H_2$)-O— | $CHF_2$ | N→O | |

TABLE 1-continued

Pyridines of the formula 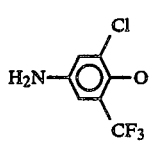

| Example | Z | $X^1$ | $X^2$ | $X^3$ | $X^4$ | —R | A | m.p. °C. b.p. °C./mbar |
|---|---|---|---|---|---|---|---|---|
| 276 | O | H | H | Cl | " | $CF_2Cl$ | N→O | |
| 277 | O | H | H | Br | " | $CF_3$ | N→O | |
| 278 | O | H | H | F | " | $CF_2CHF_2$ | N→O | |
| 279 | O | H | H | Cl | " | $CF_2CHCl$ | N→O | |
| 280 | O | H | H | Br | " | $CF_2CHFBr$ | N→O | |
| 281 | O | H | H | F | " | $CH_2CF_3$ | N→O | |
| 282 | O | H | H | Cl | " | $CF_2CHFCF_3$ | N→O | |
| 283 | O | H | H | Cl | 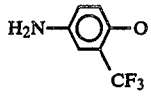 | $CHF_2$ | N | |
| 284 | O | H | H | Br | " | $CF_3$ | N→O | |
| 285 | O | H | H | F | " | $CF_2CHF_2$ | N | |
| 286 | O | H | H | Cl | " | $CF_2CHFCF_3$ | N | |
| 287 | O | H | H | F | 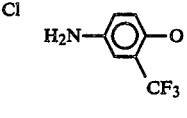 | $CF_2H$ | N | |
| 288 | O | H | H | Cl | " | $CF_3$ | N→O | |
| 289 | O | H | H | Br | " | $CF_2CHF_2$ | N | |
| 290 | O | H | H | Cl | " | $CF_2CHFCF_3$ | N→O | |
| 291 | O | H | H | F | 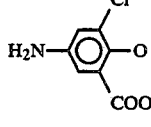 | $CF_2H$ | N | |
| 292 | O | H | H | Cl | " | $CF_3$ | N→O | |
| 293 | O | H | H | Br | " | $CF_2CHF_2$ | N | |
| 294 | O | H | H | Cl | " | $CF_2CHFCF_3$ | N→O | |
| 295 | O | H | H | F | 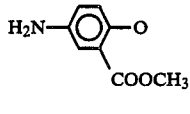 | $CF_3H$ | N | |
| 296 | O | H | H | Cl | " | $CF_3$ | N→O | |
| 297 | O | H | H | Br | " | $CF_2CHF_2$ | N | |
| 298 | O | H | H | Cl | " | $CF_2CHFCF_3$ | N→O | |

TABLE 1-continued

Pyridines of the formula I $$\begin{array}{c} X^2 \\ X^3 \diagup \diagdown Z-R \\ \| \phantom{xxx} \| \\ X^4 \diagdown \diagup X^1 \\ A \end{array}$$

| Example | Z | $X^1$ | $X^2$ | $X^3$ | $X^4$ | —R | A | m.p. °C. b.p. °C./mbar |
|---|---|---|---|---|---|---|---|---|
| 299 | O | H | H | Cl | 2,6-diCl-4-OCN-phenoxy | $CF_3$ | N | |
| 300 | O | H | H | Cl | 2,6-diCl-4-OCN-phenoxy | $CF_2H$ | N→O | |
| 301 | O | H | H | H | 2-Cl-6-CF$_3$-4-OCN-phenoxy | $CF_2CHF_2$ | N | |
| 302 | O | H | H | H | 2-Cl-6-CF$_3$-4-OCN-phenoxy | $CF_2CHFCl$ | N→O | |
| 303 | O | H | H | H | 2-Cl-6-CF$_3$-4-OCN-phenoxy | $CF_2CHFCF_3$ | N | |
| 304 | O | H | H | H | " | $CF_3$ | N→O | |
| 305 | O | H | H | H | 2-Cl-6-COOCH$_3$-4-OCN-phenoxy | $CF_2H$ | N | |
| 306 | O | H | H | H | " | $CF_2CHFCF_3$ | N→O | |
| 307 | O | H | H | H | 2-Cl-6-COOCH$_3$-4-OCN-phenoxy | $CF_2CHFCF_3$ | N | |
| 308 | O | H | H | H | " | $CHF_2$ | N→O | |

The disclosure of the commonly assigned U.S. application Ser. No. 944,323 which corresponds to German Patent Application No. P 35 45 569.1 is entitled "Pyridine derivatives, processes for the preparation thereof, agents containing same, and the use thereof as pesticides" and is filed concurrently herewith, is hereby incorporated by reference. Also, the disclosure of the commonly assigned U.S. application Ser. No. 944,324 which corresponds to German Patent Application No. P. 35 45 571.3, is entitled "Heterocyclic phenyl ethers, processes for the preparation thereof, and herbicidal agents containing same" and is filed concurrently herewith is hereby incorporated by reference.

We claim:

1. A compound of the formula I

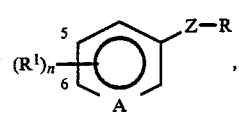

in which

A denotes N or N→O,

Z denotes O or NH,

R dentoes H, halogenated ($C_1$–$C_8$)alkyl, halogenated ($C_2$–$C_8$)-alkenyl or halogenated ($C_2$–$C_6$)alkynyl, and, for Z=0, denotes ($C_1$–$C_4$)alkoxycarbonyl, $R^1$ independently of one another denote hydrogen, halogen, amino, —NHOH, hydroxyl, or denotes a radical of the formulae Y=C=N—, $Y^1Y^2C$=N, $Y^3$NH— or

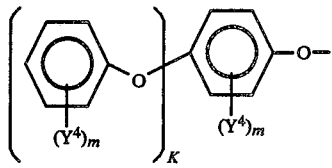

where n preferably dentoes 1 for this radical,

Y denotes O or S $Y^1$ denotes halogen, ($C_1$–$C_3$)alkylthio, ($C_1$–$C_3$)alkylsulfenyl or ($C_1$–$C_3$)alkylsulfonyl, $Y^2$ denotes a radical mentioned for $Y^1$ or mercapto, $Y^3$ denotes ($C_1$–$C_6$)alkyl or ($C_1$–$C_6$)alkylsulfenyl which may both be halogenated, phenylsulfenyl which may be substituted by ($C_1$–$C_6$)alkyl, ($C_1$–$C_6$)-alkoxy, ($C_1$–$C_6$)alkoxycarbonyl, halo($C_1$–$C_6$-alkyl), halo($C_1$–$C_6$)alkoxy, halo($C_1$–$C_6$-alkyl)carbonyl, halogen, nitro or cyano, or denotes phosphoryl or thiophosphoryl which may both be substituted by two radicals from the group comprising ($C_1$–$C_6$)alkoxy, ($C_1$–$C_6$)alkylthio, amino, ($C_1$–$C_6$)alkylamino or di($C_1$–$C_6$-alkyl)amino, $Y^4$ independently of one another, denote H, halogen, $NO_2$, $NH_2$, —$NHY^3$, —NHOH, NCO, NCS, OH, ($C_1$–$C_6$)alkyl, ($C_2$–$C_6$)alkenyl, ($C_2$–$C_6$)alkynyl, ($C_1$–$C_6$)-alkoxy, or ($C_1$–$C_6$)alkoxycarbonyl, where the last five radicals mentioned may be halogenated, or denotes nitro, cyano, carboxy or a carboxylate salt, K denotes 0 or 1, m and n, independently of one anotherr, denote a number from 1 to 4, with the proviso that n does not denote 0 when Z-R denote OH or $NH_2$, and at least one radical $R^1$ denotes a radical of the formula

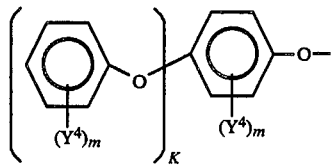

or $(R^1)_n$ represent two radicals in the 5 or 6 position of the heterocyclic ring, whereby $R^1$ in the 5 position is halogen and in the 6 position is a radical of the group consisting of halogen, amino, or hydroxyl.

2. A compound of the formula I of claim 1, in which

A denotes N or N→O,

Z denotes O or NH,

R denotes H or halogenated ($C_1$–$C_8$)alkyl, $R^1$ independently of one another denote hydrogen, halogen, amino, hydroxyl, phenylazo which may be mono- or polysubsituted in the phenyl ring by halogen, nitro or carboxyl, or denotes a radical of the formulae Y=C=N—, $Y^1Y^2C$=N— or

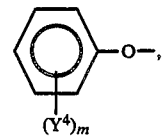

Y dentos O or S, $Y^1$ dentoes halogen or ($C_1$–$C_3$)alkylthio, $Y^2$ denotes a radical mentioned for $Y^1$ or mercapto, $Y^4$, independently of one another, denote H, $NO_2$, $NH_2$, —NHOH, halogen, —NCO, NCS, OH, ($C_1$–$C_6$)alkyl, or ($C_1$–$C_6$)alkoxycarbonyl, where the five last mentioned radicals may be halogentated, and m and n, independently of one another, denote a number from 1 to 4.

3. A compound of the formula I

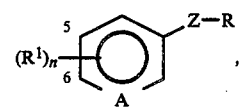

in which

A denotes N,

Z denotes O or NH,

R denotes H or halogenated ($C_1$–$C_4$)alkyl, $R^1$ denotes H, halogen, amino, hydroxyl or

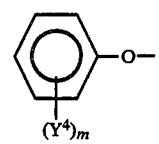

$Y^4$ denotes H, Cl, $CF_3$, $NH_2$, —NCO or ($C_1$–$C_2$)alkoxycarbonyl, which are oriented in the 2, 4 or 6 position of the phenoxy radical, and m and n denote a number from 1 to 3.

4. A herbicidal composition comprising a herbicidally effective amount of a compound according to claim 1 and a herbicidally acceptable carrier.

* * * * *